United States Patent [19]

Lavanish et al.

[11] 4,449,998

[45] May 22, 1984

[54] HERBICIDALLY ACTIVE OXADIAZOLE UREAS

[75] Inventors: Jerome M. Lavanish, Akron; Barry Van Gemert, Massillon, both of Ohio

[73] Assignee: PPG Industries, Inc., Pittsburgh, Pa.

[21] Appl. No.: 380,191

[22] Filed: May 20, 1982

[51] Int. Cl.³ .................... C07D 271/06; A01N 43/82
[52] U.S. Cl. ............................................ 71/92; 548/133
[58] Field of Search ............................. 548/133; 71/92

[56] References Cited

U.S. PATENT DOCUMENTS

| | | | |
|---|---|---|---|
| 3,454,591 | 7/1969 | Schulz et al. | 260/306.8 |
| 3,564,606 | 2/1971 | Breuer et al. | 548/133 |
| 3,759,940 | 9/1973 | Krenzer | 260/306.8 |
| 3,822,280 | 7/1974 | Moser et al. | 548/133 |
| 3,922,160 | 11/1975 | Buttimore | 71/90 |
| 4,353,920 | 10/1982 | Gay | 548/133 |

*Primary Examiner*—Mary C. Lee
*Attorney, Agent, or Firm*—Edward J. Whitfield

[57] ABSTRACT

This invention concerns certain 3-(5-substituted-1,2,4-oxadiazol-3-yl)-1,1-substituted ureas having herbicidal activity, and their use to control weeds.

6 Claims, No Drawings

HERBICIDALLY ACTIVE OXADIAZOLE UREAS

FIELD OF THE INVENTION

This invention concerns certain oxadiazole ureas, and in particular, 3-(5-substituted-1,2,4-oxadiazol-3-yl)-1,1-substituted ureas having herbicidal activity, and their use to control weeds.

DESCRIPTION OF THE INVENTION

This invention relates to 3-(5-substituted-1,2,4-oxadiazol-3-yl)-1,1-substituted ureas represented by the formula:

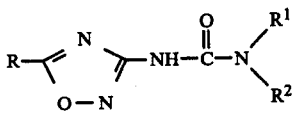

wherein R is alkyl of up to 6 carbon atoms; cycloalkyl of from 3 to 8 carbon atoms; alkenyl or alkynyl of up to 5 carbon atoms; $-R^3-O-R^4$ or $-R^3-S-R^4$ wherein $R^3$ is alkylene of up to 6 carbon atoms and $R^4$ is alkyl of up to 6 carbon atoms; or

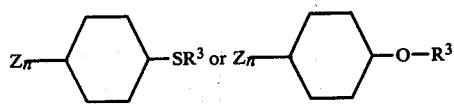

wherein:
Z is nitro, halogen, trifluoromethyl or $R^4$, and n is 0, 1, 2, or 3; and
$R^1$ and $R^2$ are hydrogen or the same or different alkyl or alkoxy of up to 6 carbon atoms, provided that only one of $R^1$ or $R^2$ may be hydrogen.

Some alkyl groups of which the various constituents in the above formula are representative are, for example, methyl, ethyl, n-propyl, isopropyl, n-butyl, isobutyl, sec-butyl, tert-butyl, pentyl, hexyl, or the like. Exemplary alkoxy groups are methoxy, ethoxy, propoxy, butoxy, methoxy-ethyl, and the like. As examples of cycloalkyl groups there may be mentioned cyclopropyl, cyclobutyl, cyclopentyl, cyclohexyl, cycloheptyl, and cyclooctyl. Allyl, butenyl, pentenyl, propynyl, butynyl, pentynyl, and the like are exemplary of suitable alkenyl and alkynyl groups represented in the above formula. Representative suitable alkylene groups are, for example, methylene, ethylene, propylene, butylene, pentylene, or hexylene. As the halogen substituents, there may be mentioned chlorine, bromine, iodine, or fluorine, preferably chlorine or bromine.

Although any compound within the scope of the above formula is believed to have herbicidal activity in accordance with this invention, those compounds that have been found to be especially efficacious are 3-(5-t-butyl-1,2,4-oxadiazol-3-yl)-1,1-dimethyl urea and 3-(5-t-butyl-1,2,4-oxadiazol-3-yl)-1-methyl-1-methoxy urea.

The compounds of this invention may be conveniently prepared by phosgenating a 5-substituted-3-amino oxadiazole of the formula:

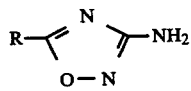

wherein R is as previously defined to prepare the corresponding isocyanate. Alternatively, the amino oxadiazole may be reacted with phenyl chloroformate to prepare the corresponding phenyl carbamate. The isocyanate or carbamate is then reacted with an equivalent amount of an appropriately substituted amine of the formula:

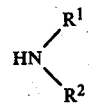

wherein $R^1$ and $R^2$ are as previously defined, to form a compound of the invention.

The following Examples are illustrative of the synthesis of certain specific compounds of this invention.

EXAMPLE 1

Preparation of 3-(5-t-butyl-1,2,4-oxadiazol-3-yl)-1-methyl-1-methoxy urea

To a 500 milliliter round bottom flask containing 200 milliliters of ethyl acetate saturated with phosgene was added dropwise, with continuous stirring, 20 grams of 3-amino-5-t-butyl-1,2,4-oxadiazole. The reaction mixture was stirred overnight (about 16 hours) at room temperature and then purged with nitrogen for 24 hours to remove unreacted phosgene. The clear solution was then stripped on a rotary evaporator to give 23 grams of a clear, light yellow oil. The oil was diluted with 150 millimeters of benzene and 10 grams of methoxymethyl amine was added dropwise, with continuous stirring. Exothermic heating was noted as well as formation of an amine hydrochloride precipitate. The reaction mixture was then heated to reflux, maintained at reflux for 2 hours, cooled in an ice-bath and filtered to remove the amine hydrochloride precipitate. The filtrate was stripped on a rotary evaporator to give a light yellow oil. The oil was crystallized from petroleum ether, filtered and dried giving 24.6 grams of solid material identified by IR and NMR spectroscopy as the desired product, 3-(5-t-butyl-1,2,4-oxadiazol-3-yl)-1-methyl-1-methoxy urea.

EXAMPLE 2

Preparation of 3-(5-t-butyl-1,2,4-oxadiazol-3-yl)-1,1-dimethyl urea

This compound is prepared following the procedure described in Example 1 except that dimethylamine is used in place of methoxymethyl amine.

The mode of synthesis of specific compounds of this invention have been illustrated by the foregoing Examples; but, it is to be understood that any compound contemplated within the scope of this invention may be prepared by those skilled in the art simply by varying the choice of starting materials and using the illustrated techniques or other suitable techniques.

The compounds of this invention have been found effective in regulating the growth of a variety of undesirable plants, i.e., weeds, when applied in an herbicidally effective amount to the growth medium prior to emergence of the weeds or to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors such as, for example, hardiness of a particular weed species, extent of weed infestation, climatic conditions, soil conditions, methods of application, and the like. Typically, as little as 1.0 or less pound acre to 10 or more pounds per acre of compound or mixtures of compounds may be required. Of course, the efficacy of a particular compound against a particular weed species may readily be determined by relatively straightforward laboratory or field testing in a manner well known to the art.

The compounds of this invention may be used as such or in formulation with agronomically acceptable adjuvants, inert carriers, other herbicides, or other commonly used agricultural compounds, for example, pesticides, stabilizers, safeners, fertilizers, and the like. The compounds of this invention, whether or not in formulation with other agronomically acceptable materials, are typically applied in the form of dusts, granules, wettable powders, solutions, suspension, aerosols, emulsions, dispersions or the like, in a manner well known to the art. When formulated with other typically used agronomically acceptable materials, the amount of compound or compounds of this invention present in the formulation may vary over a wide range, for example, from about 0.05 to about 95 percent by weight on weight of formulation. Typically, such formulations will contain from about 5 to about 75 percent by weight of compound or compounds of this invention.

The compounds of this invention as exemplified by the compounds of Examples 1 and 2, have been found effective in controlling a variety of broadleaf and grassy weeds particularly when applied preemergence. The compounds prepared according to Examples 1 and 2 were tested for herbicidal activity against various weed species under controlled laboratory conditions of light, temperature, and humidity, using techniques known to the art. In preemergence evaluation, a solvent solution of the test compound is applied at the desired rate to the weed species prior to emergence from the growth medium, the toxic effect of the compound being determined by visual inspection periodically after application.

Each of the compounds of Examples 1 and 2 were individually applied preemergence at an application rate of 2 pounds per acre to common broadleaf and grassy weeds, namely teaweed (*Sida spinosa*), jimson weed (*Datura stramonium*), wild mustard (*Brassica kaber*), yellow nutsedge (*Cyperus esculentus*), yellow foxtail (*Setaria glauca*), large crabgrass (*Digitaria sanguinalis*), johnsongrass (*Sorghum halepense*), coffeeweed (*Daubentonia punicea*), velvetleaf (*Abutilon theophrasti*), tall morningglory (*Ipomoea purpurea* Roth), wild oats (*Avena fatua*), barnyardgrass (*Echinochloa crusgalli*), and cotton, var. DeltaPine 61 (*Gossypium hirsutum*).

Herbicidal efficacies were determined by visual inspection periodically after application and a Numerical Injury Rating assigned, based on a scale of 0 (no injury) to 10 (all plants dead). The following Table gives the Numerical Injury Ratings for the various weed species against which the compounds of Examples 1 and 2 were tested. The Numerical Injury Ratings were determined twenty two (22) days after preemergence application of the compound of Examples 1 and 2 at a rate of two (2) pounds per acre.

TABLE

| | Preemergence Herbicidal Activities of the Compounds of Examples 1 and 2 | |
|---|---|---|
| Weed Species | Example 1 | Example 2 |
| Teaweed | 10 | 10 |
| Jimsonweed | 10 | 9 |
| Wild mustard | 10 | 10 |
| Yellow nutsedge | 0 | 2 |
| Yellow foxtail | 9 | 10 |
| Large crabgrass | 9 | 10 |
| Velvetleaf | 10 | 10 |
| Johnsongrass | 3 | 10 |
| Coffeeweed | 9 | 10 |
| Tall morningglory | 10 | 10 |
| Wild oats | 9 | 10 |
| Barnyardgrass | 8 | 10 |

We claim:

1. A compound represented by the formula:

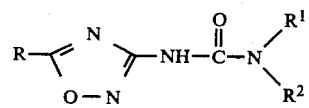

wherein R is alkyl of up to 6 carbon atoms; cycloalkyl of from 3 to 8 carbon atoms; alkenyl or alkynyl of up to 5 carbon atoms; $-R^3-O-R^4$ or $R^3-S-R^4$ wherein $R^3$ is alkylene of up to 6 carbon atoms and $R^4$ is alkyl of up to 6 carbon atoms; or

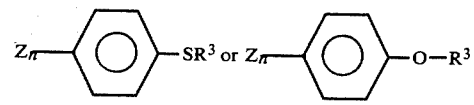

wherein:
  Z is nitro, halogen, trifluoromethyl or $R^4$, and n is 0, 1, 2, or 3; and
  $R^1$ and $R^2$ are hydrogen or the same or different alkyl or alkoxy of up to 6 carbon atoms, provided that only one of $R^1$ or $R^2$ may be hydrogen.

2. The compound of claim 1 wherein R is alkyl.

3. The compound of claim 2 wherein R is tertiary butyl.

4. A compound of claim 3 selected from 3-(5-t-butyl-1,2,4-oxadiazol-3-yl)-1,1-methyl urea or 3-(5-t-butyl-1,2,4-oxadiazol-3-yl)-1-methyl-1-methoxy urea.

5. A herbicidal composition containing an agronomically acceptable carrier and a herbicidally effective amount of a compound or mixture of compounds defined in claim 1.

6. In a method controlling weed growth wherein a herbicidally effective amount of a herbicide is applied to a growth medium prior to emergence of weeds from or applied to the weeds subsequent to emergence from the growth medium, wherein the improvement resides in using as the herbicide a herbicidally effective amount of a compound or mixture of compounds defined in claim 1.

* * * * *